US008630868B2

(12) United States Patent
Coutinho et al.

(10) Patent No.: US 8,630,868 B2
(45) Date of Patent: Jan. 14, 2014

(54) METHOD AND SYSTEM TO EXCHANGE INFORMATION ABOUT DISEASES

(75) Inventors: Marcelo P. Coutinho, Itaperuna (BR); Fabricio F. Costa, Chicago, IL (US); Luciano S Foly, Itaperuna (BR)

(73) Assignee: Datagenno Interactive Research Ltda. (BR)

( * ) Notice: Subject to any disclaimer, the term of this patent is extended or adjusted under 35 U.S.C. 154(b) by 106 days.

(21) Appl. No.: 12/951,060

(22) Filed: Nov. 21, 2010

(65) Prior Publication Data

US 2012/0130740 A1    May 24, 2012

(51) Int. Cl.
*G06Q 10/00*        (2012.01)
*G06Q 50/00*        (2012.01)

(52) U.S. Cl.
USPC .................................................. 705/2; 705/3

(58) Field of Classification Search
USPC ........................................................ 705/2–3
See application file for complete search history.

(56) References Cited

U.S. PATENT DOCUMENTS

| | | | |
|---|---|---|---|
| 2006/0143043 A1* | 6/2006 | McCallie et al. | 705/2 |
| 2006/0149591 A1* | 7/2006 | Hanf et al. | 705/2 |
| 2008/0059249 A1* | 3/2008 | Joao | 705/3 |
| 2009/0089090 A1* | 4/2009 | Schoenberg | 705/2 |
| 2010/0312798 A1* | 12/2010 | Dutta et al. | 707/780 |
| 2010/0332258 A1* | 12/2010 | Dahlke et al. | 705/3 |

* cited by examiner

*Primary Examiner* — Joseph Burgess
(74) *Attorney, Agent, or Firm* — Omar D. Galaria; Baker & McKenzie LLP (57) ABSTRACT

An online system and method enabling users to exchange information and establish collaboration in scientific projects on rare diseases is described. The website allows users to create a list of symptoms for a patient with a rare disease who is under their care. The patient's list of symptoms is then used to find other patients sharing a similar list of symptoms. A matching system creates a match report that ranks patients with similar symptoms. Once a list of potential matches is available, the user may take the initiative of contacting other colleagues with similar clinical cases under their care, for the purpose of exchanging information and/or establishing collaboration in scientific projects about a particular rare disease. A database containing information on rare diseases, along with other services, is also provided to the users at the website.

13 Claims, 7 Drawing Sheets

METHOD AND SYSTEM TO EXCHANGE INFORMATION ABOUT DISEASES

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Technical Field

The invention relates generally to the operation of an online service or website that helps in establishing scientific collaboration between users interested in studying rare diseases, and more specifically to a matching system designed to find users who have patients that share similar lists of symptoms under their care.

2. Description of Related Art

According to the National Institutes of Health (NIH)'s Genetic and Rare Diseases Information Center (GARD), there are more than 7,000 rare diseases. A disease is considered rare if fewer than 200,000 people in the United States have it. About 25 million Americans have a rare disease. Many rare diseases are caused by changes in genes and are called "genetic diseases".

Physicians will sometimes say that a child has an "undiagnosed rare condition" or an "undiagnosed genetic condition" when they are unable to find a diagnosis for certain characteristics or symptoms. In fact, finding an underlying diagnosis for many conditions can be a very long and frustrating experience. A diagnosis can take as many as five years, and occasionally may never happen, especially with rare conditions.

This can be very difficult for parents, who sometimes want to know if their child should be evaluated by a rare disease specialist. Unfortunately, because there usually are so few cases of specific rare diseases, there is often not a doctor who has seen many (or any) similar cases. For this reason, it may take a doctor a long time to match symptoms to a possible diagnosis.

Although there has been great progress in the Clinical Genetics field in recent years, rare cases often end up in careful clinical case and family history descriptions, and physical exam, looking at the standard laboratory data and trying to put all clinical features together to come up with some sort of diagnostic probability. Even after a battery of standard genetic screenings, 30 to 40 percent of patients with morphological abnormalities, for example, do not have a precise diagnosis.

Detailed genetic analyses and studies are hardly ever undertaken on such rare cases unless patients with similar symptoms can be identified and scientists with related projects can collaborate with each other. In addition, clinical and molecular information on rare diseases are spread out in the literature and all over the internet, in a plethora of public and private websites, making difficult for medical and healthcare professionals to quickly translate the latest advances into effective clinical intervention.

Currently existing online health information portals provide health information services to consumers, physicians, healthcare professionals, employers, and health plans. However, they only cover a group of well-known genetic diseases. Public, government, not-for-profit, and non-commercial websites and databases that provide medical and health information are usually diverse and rich in content but offer a very limited degree of interaction for their users to exchange information. Online medical communities allow professionals to discuss medications and procedures, exchange ideas and seek for information about treatments, and collaborate in clinical cases. However, discussion forums and groups are often limited to text messaging and chat rooms making it difficult to follow them as they grow in number of participants and posted comments.

Thus, there is a need for an online service, website or portal which allows physicians, allied health personnel, and scientists interested in rare diseases to find patients sharing similar symptoms and colleagues with whom they might collaborate and/or share information on related projects. It is also desirable that this same website provides complementary services that include, for example, access to a database containing clinical and molecular information about rare diseases.

BRIEF SUMMARY OF THE INVENTION

A website (or portal) provides a system and method for matching users interested in studying and/or sharing information about a particular rare disease, based on lists of symptoms of patients under their care. The matching system determines which users potentially share the same clinical and/or scientific interests by comparing the list of symptoms of patients they have under their care. A rare diseases database, along with other services, is also provided to the users at the website.

In the present invention, the website provides a matching system where potential matches are based on the list of symptoms of patients with rare diseases. Hence, patients with similar symptoms can be found and users with these patients under their care may contact and collaborate with each other, allowing detailed analysis and studies to be undertaken on such rare cases. Other services provided at the website, for example, a database containing current clinical and molecular information about rare diseases, may help users to quickly translate the latest scientific and medical advances into an effective clinical intervention. It may also facilitate research on rare diseases. Further objects and advantages will become apparent from a consideration of the ensuing description and drawings.

DETAILED DESCRIPTION OF THE INVENTION

In an embodiment, the website is provided by a system including a server that is coupled to the Internet along with associated software that provides the matching system to users along with other services.

In another embodiment, the website users register and keep in a database their profiles that include personal and professional information, e. g., their name, birth date, gender, photo, address, e-mail, phone number, medical specialty, academic degrees, job position, job address, bio sketch, résumé, research interests and so forth. Users may also store in the user database clinical and/or research data as part of the user profile. This includes imaging exam results, pathology test results, clinical trial results, molecular diagnostic results, research results and so forth.

In a preferred embodiment, still as part of the user profile, the user is also allowed to create and store in the user database a list of symptoms for each patient with a rare disease who is under his/her care. The list of symptoms of a patient includes, but is not limited to, signs, manifestations, presentations, aspects, test results, and so forth.

In another preferred embodiment, the list of symptoms of a patient may be used by the user to find other patients with similar lists of symptoms and, consequently, the colleagues with these similar clinical cases under their care. A matching system then provides to the user a matching list that ranks patients with similar symptoms. Once the matching results is available, the user may takes the initiative of contacting other colleagues with similar clinical cases under their care, for the purpose of exchanging information and/or establishing scientific collaboration about that particular rare disease. The matching system can be implemented using methods for list matching well known in the art, e.g., those used in match making services intended to promote people's relationship and dating.

In another embodiment, the website provides communication mechanisms well known in the art for communication among its users. Users who are simultaneously accessing the system can establish a real time, instant messaging, voice, or voice and video communication session. A contact can also be made asynchronously when a user sends text, voice, video or graphical messages to another user via e-mail, or via a mechanism that may be provided by the system, such as a local "inbox". Once the second user responds in a likely manner, a two-way communication is established whereby the two users may start a scientific collaboration and/or exchange data.

In another embodiment, the website may include a database containing, but not limited to, clinical and molecular information about rare diseases. The database is a tool to help users find current information about rare diseases as a support for clinical diagnosis and research. This may involve various forms of information storage and retrieving by electronic means well known in the art.

In yet another embodiment, the website may provide users with a computerized diagnostic tool to assist physicians during a patient examination. The tool may help early detection and treatment of rare diseases in the daily routine. This may involve various forms and methods of automation including, but not limited to, static procedures or algorithms and list-based processing well known in the art.

In another embodiment, the website may provide access to scientific and technical literature. Easy and continuous access to fresh information is important for the progressing of research projects and studies on rare diseases. This may be achieved through other third party websites, such as Science-Direct (http://www.sciencedirect.com).

In another embodiment, the website may, provide educational tools for improving medical education, more specifically in the rare diseases field. This may involve, but is not limited to, providing courses or training on rare diseases and their diverse aspects such as clinical and molecular. It may be implemented as an audiovisual Macromedia Flash file in the .swf format, with animated text and textual effects, sound, and interactive features such as the display of text, video or picture in response to the user positioning a cursor over a given text or icon and clicking a mouse button. Other familiar audio, video, or audiovisual computer-based presentation technologies may also be used, as may other forms of user I/O (input/output) and user interactivity.

In another embodiment, healthcare related information may also be provided in the web interface of the present invention. This may be through other websites, e.g., electronic prescription and electronic medical/health record websites.

In a further embodiment, the website may provide marketing tools. The marketing tools may be used by the website to promote its and/or third party products and services to current and prospective users. This may take many forms including, but not limited to, e-mail campaigns, internet advertising, and/or advertising space on a web interface of the present invention.

Additional explanation of some of the terms used herein will assist the understanding of the present invention.

Throughout this document, "user"/"users" is/are, but not limited to, physicians, allied health personnel, scientists and others in the healthcare field.

Throughout this document, "symptoms" can be defined as signs, manifestations, presentations, aspects; patient basic information (e.g., age, sex); patient history (e.g., prior illnesses, parental health information); history of patient complaints and progress; physical signs (e.g., vital signs) and the results of self- or assisted-physical examination maneuvers; lab and test results; results of an imaging modality of choice, and so forth.

The following detailed description presents a description of certain specific embodiments of the present invention. However, the present invention may be embodied in a multitude of different ways as defined and covered by the claims. In this description, reference is made to the drawings wherein like parts are designated with like numerals throughout.

Figure 1:
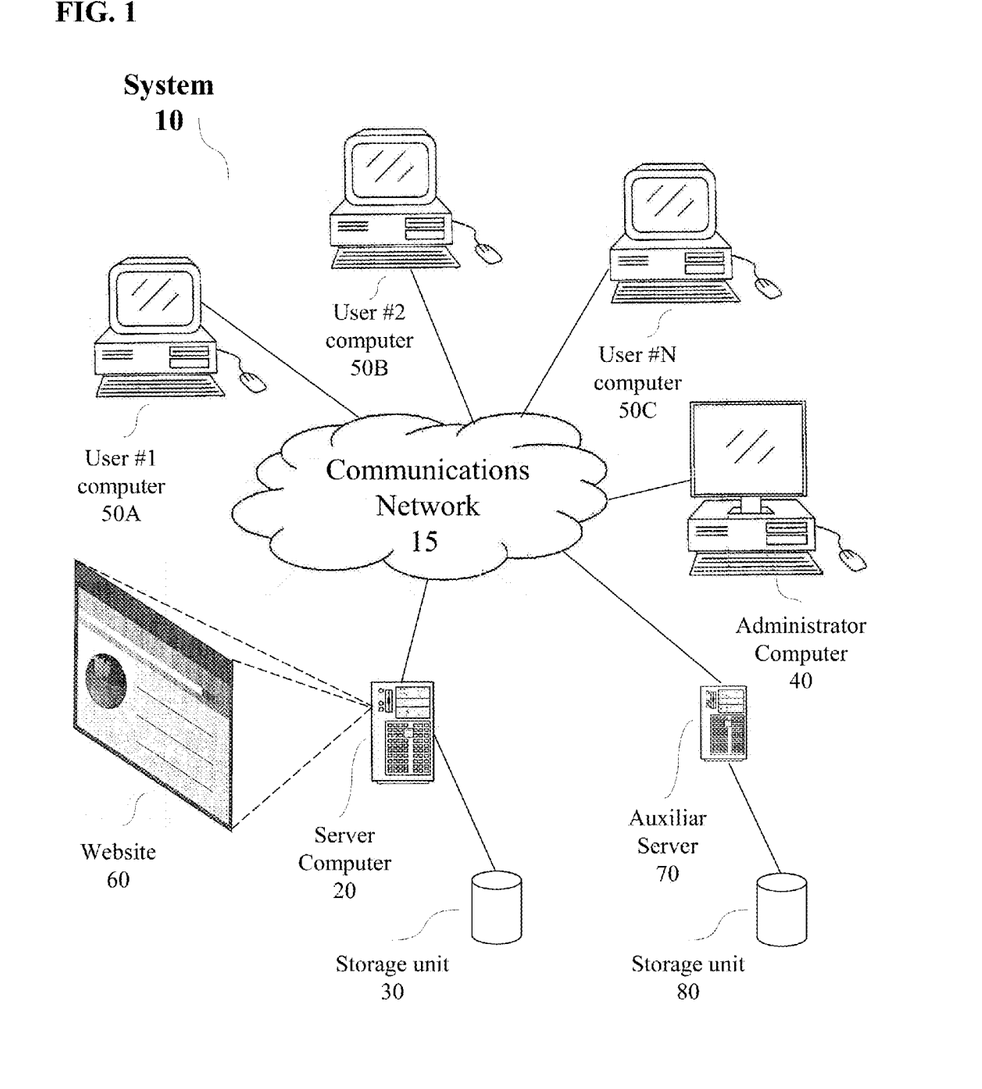
FIG. 1 illustrates a pictorial representation of a system by means of which the present invention may be implemented.

With reference now to the figures, FIG. 1 is a pictorial representation of a network data processing system in which the present invention may be implemented. Network data processing system 10 is a network of computers in which the present invention may be implemented. The system 10 includes a communications network 15, providing communication between a server computer 20 with storage unit 30, one or more service administrator computers 40, and a plurality of user computers 50A-C. The server 20 provides operating system, data, and applications for the users 50A-C. The server computer 20 includes one or more processing elements and software applications. The system 10 includes a website 60 to provide services to users 50A-C. The website 60 and the services are provided by the server 20. The system 10 might also contain a supplementary server computer 70 and additional data storage unit 80.

Suitable communications network 15 include, but are not limited to, the Internet, ethernet, intranet, extranet, a virtual private network (VPN), and non-TCPI-IP based networks. The communications network 15 may include connections, such as wire, wireless communication links, of fiber optic cables.

Suitable user computer units 50A-C include desktop personal computers, personal digital assistants (PDAs), laptops, notebooks, cell phones, tablet computers (e.g., iPad), Internet-enabled televisions, or any other device capable of interfacing with a communications network.

Those of ordinary skill in the art will appreciate that the hardware depicted in FIG. 1 may vary. The depicted example is not meant to imply architectural limitations with respect to the present invention.

Figure 2:
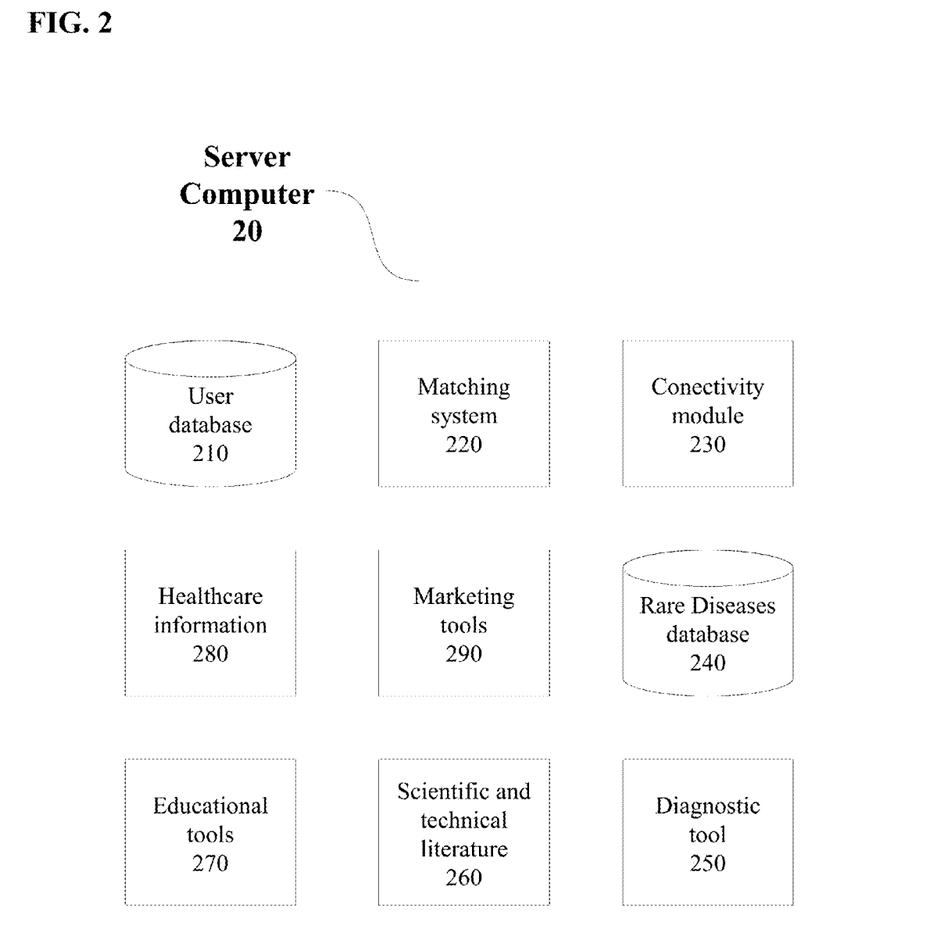
FIG. 2 illustrates the services provided by the system to the users through the website in accordance with the present invention.

FIG. 2 illustrates the services that may be provided by the system 10 through the server 20. The website 60 provides users with access to the services provided by the system 10. The website 60 provides users with: access to a user database 210 where they may store personal and professional data, clinical and research data as well as lists of symptoms created for patients under their care; access to a list matching system 220 designed to find other patients with lists of symptoms similar to the ones of patients under his/her care; access to a connectivity module 230 with a suite of options that allows a user to take the initiative of contacting other users for the purpose of communicate and share information; access to a rare diseases database containing clinical and molecular information about these diseases 240; access to a computerized diagnostic tool 250 to assist physicians during a patient examination; access to scientific and technical literature 260 provided by other websites; access to educational tools 270 that provide courses or training on rare diseases; access to healthcare related information 280 through other websites, e.g. electronic prescription and electronic medical/health records websites; and marketing tools 290 that may be used by the website to promote its and/or third party products and services to current and prospective users.

Figure 3:
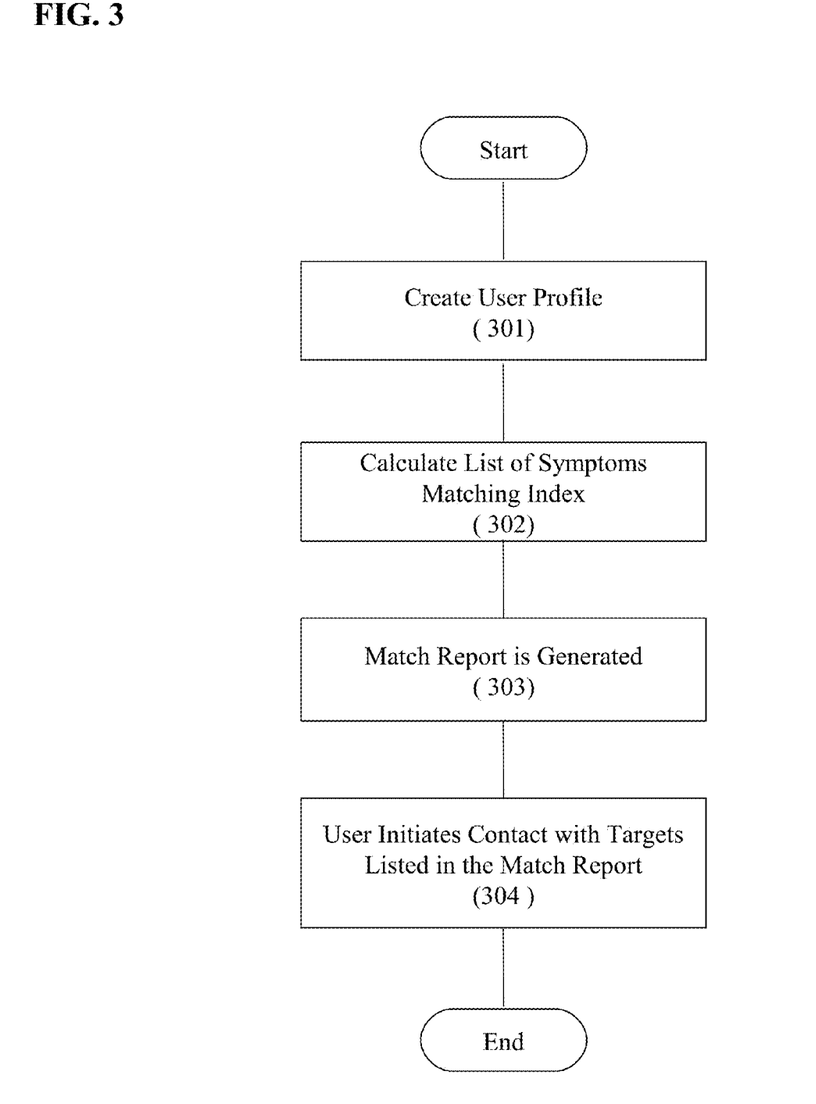
FIG. 3 is a flowchart illustrating an overview of the list of symptoms-based scientific collaboration matching system in accordance with the present invention.

FIG. 3 is a flowchart illustrating an overview of the list of symptoms-based scientific collaboration matching system in accordance with the present invention. When the user enters the website and begins the process, the first step is to create a profile (step 301) that includes personal and professional background information, storing clinical and/or research data, and creating a list of symptoms for each patient under his/her care. Data associated with each user, such as the user 50A, are stored at user database 210.

Figure 4:
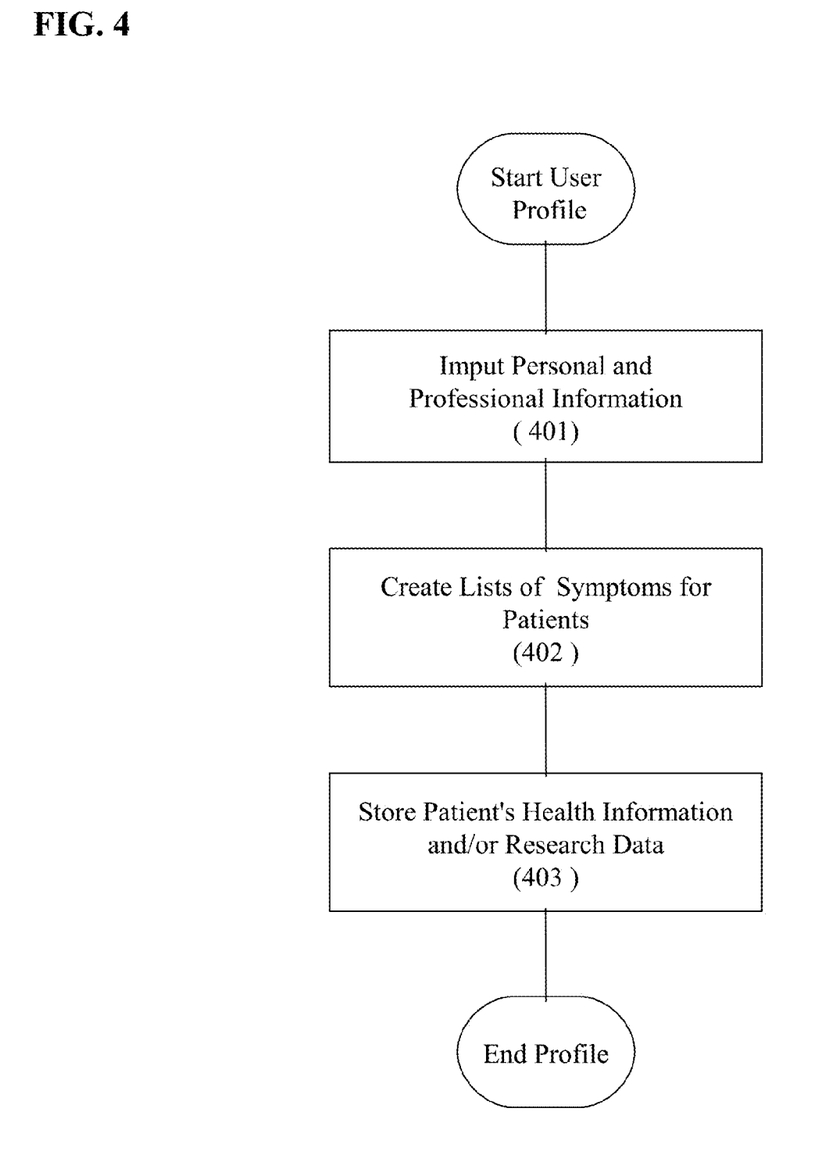
FIG. 4 is a flowchart illustrating in more detail the process by which a user profile is created in accordance with the present invention.

FIG. 4 is a flowchart illustrating in more details the process by which a user profile is created in accordance with the present invention. The user begins by supplying personal and professional information about him or her self (step 401). After supplying the relevant personal and professional information, the user also has the opportunity to create a list of symptom for each patient under his/her care (step 402). In addition, the user may stores patient's health information and/or research data (step 403) that he/she may eventually want to share with other users. The lists of symptoms of patients can be created by selecting symptoms from a list of symptoms.

In an alternative embodiment, users may create lists of symptoms for patients entering symptoms by their selves. In the end, each list of symptom is associated with a patient, and each patient is associated with a user.

Returning to FIG. 3, once the user profile is created and lists of symptoms of patients are entered by the user, a list matching engine module may be employed to search for potential matches among target lists of symptoms stored in the user database 210 in step 302. The matching system compares the list of symptoms entered by the user with target lists of symptoms using well-known list matching algorithms and methods in the art. In step 303, the match engine generates a match report that ranks the targets according to how well they match the list of symptoms entered by the user. After reviewing the information presented in step 303, the user may contact one or more of the individuals ranked in the match report using the connectivity module 230 in step 304.

The connectivity module 230 provides a suite of options that allows the user to take the initiative of contacting a second user from the match report for the purpose of communicate and share clinical and scientific information about medical cases they have in common. The options may include:

1) Allowing two users who are simultaneously accessing the system to establish a real time, instant messaging, voice, or voice and video communications session.

2) Allowing a user to asynchronously send text, voice, video or graphical messages to another user, who is a potential collaborator, or via e-mail by means of a local "inbox". Then allowing the second user to respond in a likely manner, so that a two-way communication is established whereby the two users may begin to establish collaboration and share data.

Figure 5:
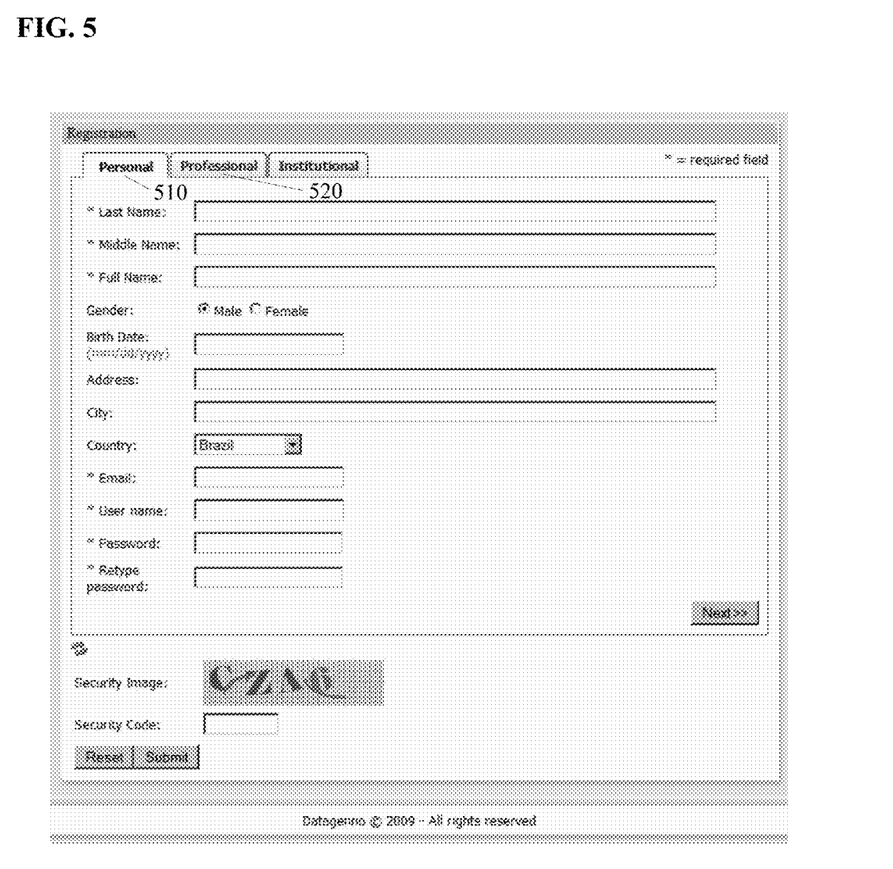
FIG. 5 illustrates an exemplary graphical user interface provided by the website as part of the process of registering new users.

FIG. 5 illustrates an exemplary graphical user interface provided by the website as part of the process of registering new users. Personal information 510 includes, but is not limited to, name, birth date, gender, photo, address, e-mail, and phone number. Professional information 520 includes, but is not limited to, medical specialty, academic degrees, job address, job position, bio sketch, résumé, research interests, publications, press releases, past and ongoing research projects.

Figure 6:
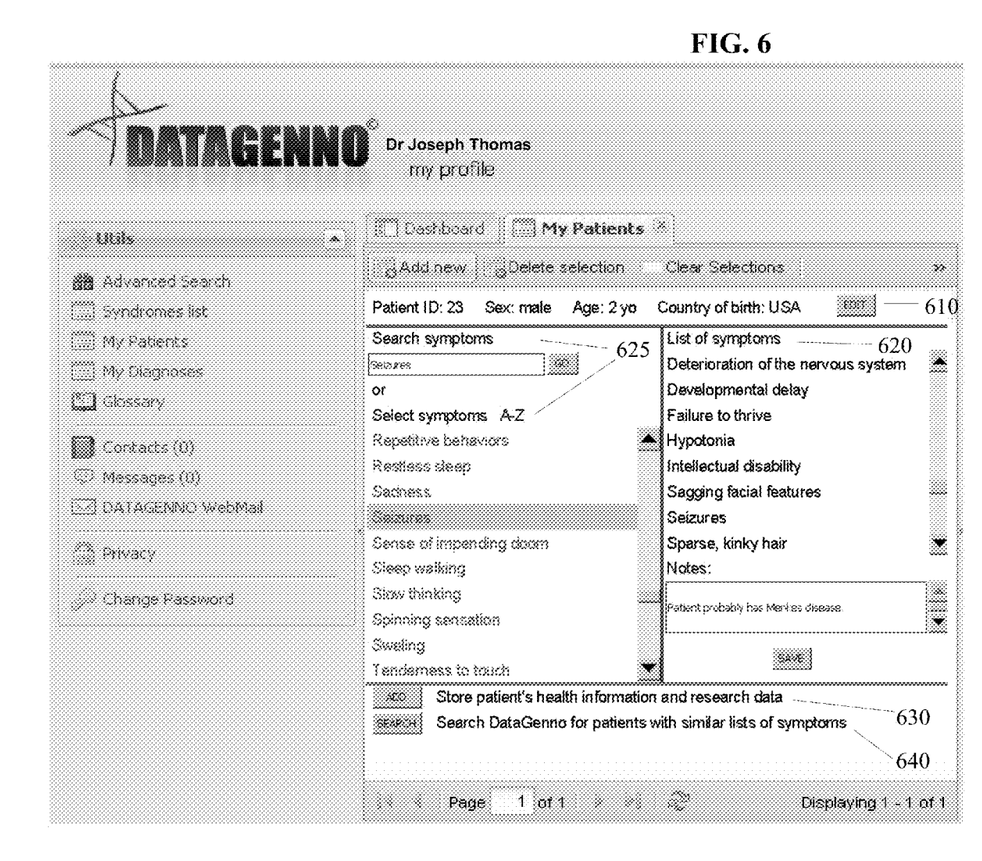
FIG. 6 illustrates an exemplary graphical user interface provided by the website for creating lists of symptoms of patients, storing clinical and research data, and search for patients with similar lists of symptoms.

FIG. 6 illustrates an exemplary graphical user interface provided by the website for creating lists of symptoms of patients, storing clinical and research data, and search for patients with similar list of symptoms. The user starts the process by entering patient's basic information 610 (e.g., identification, age, sex). Then, a list of symptom 620 for the patient may be created by picking symptoms from a list of symptoms 625 that includes, but is not limited to, signs, manifestations, presentations, and aspects. Additionally, the user may store 630 clinical and research data related to the patient or to the disease. This includes, but is not limited to, patient history (e.g., prior illnesses, parental health information); history of patient complaints and progress; physical signs (e.g., vital signs) and the results of self- or assisted-physical examination maneuvers; laboratory and test results; results of an imaging modality of choice, molecular diagnostic results; clinical trial results, and laboratory research results. Once the list of symptoms is created, it may be used to search 640 for patients with similar lists of symptoms.

Figure 7:
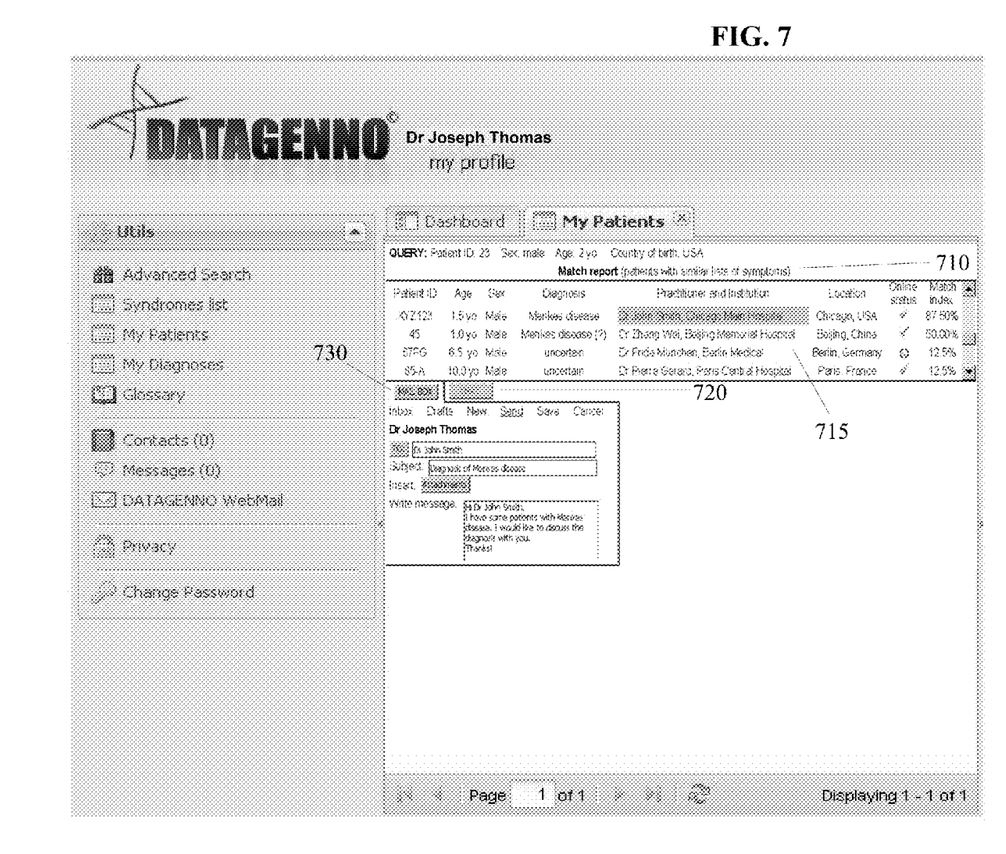
FIG. 7 illustrates an exemplary graphical user interface provided by the website for displaying a match report generated as result of a search for patients with similar lists of symptoms.

FIG. 7 illustrates an exemplary graphical user interface provided by the website for displaying a match report generated as result of a search for patients with similar lists of symptoms. The list matching engine generates a match report 710 that ranks the targets according to how well they match the list of symptom 620 entered by the user. The user may then contact one or more of the users 715 ranked in the match report 710. The contact can be done using the connectivity module 230 that provides real time and asynchronous communication means like live online chat 720 and mail box 730.

Suitable implementations of the exemplary graphical user interfaces shown in FIGS. 5-7 include, but are not limited to, web browser interfaces such as HTML, Java interfaces, and any other interfaces implemented in a computer programming or specification language.

Additional alternative embodiments of the present invention are listed below:

The present invention may be used not only for rare diseases but also for any kind of diseases where scientific collaboration and/or sharing information might be necessary, for example, to develop new treatments, clinical procedures, forms of intervention, and drugs. This may include cancer, neurological, and heart diseases.

The present invention may also provide the option of searching for individuals based solely on the user's personal and professional information. This may include name, job address, medical specialty, research area, and so forth.

The connectivity module 230 of the present invention may also provide online discussion forums for group-based communication among its users to share experience with other users. These shared experiences may not be reserved for matched individuals only, but also for users who share other interests.

The present invention may also be used by parents and patients to learn about a specific disease, possible treatments, etc. Parents and patients may also use the website to share their experiences bringing together other people and patient advocates in an effort to fight a particular rare disease or rare diseases in general.

The present invention may also be used by the physicians and allied health personnel to assist in educating patients about their condition, possible treatments, etc. The medical professional can refer the patient to particular sections of interest to the patient's condition, allowing the patient to later read more information and refer back the information if questions later arise.

While the present invention has been described regarding a specific embodiment thereof, it will be apparent to those skilled in the art that numerous alternatives or modifications are possible. Accordingly, the embodiment disclosed in this application is to be considered as illustrative and not limiting. Various changes can be made without departing from the spirit and scope of the invention as set forth in the appended claims.

What is claimed is:

1. A method for generating a list of target patients, the method comprising:
   receiving, at a network server, a request to generate the list of target patients, the request including an identified list of symptoms associated with an identified patient of a first healthcare professional;
   comparing, at the network server, at least one symptom from the identified list of symptoms against at least one target list of symptoms, wherein each target list of symptoms is associated with one target patient; and
   generating, at the network server, the list of target patients including a matching index for at least one target patient in the generated list, wherein the matching index comprises a numerical value representative of the similarity between the identified list of symptoms with the target list of symptoms;
   ranking, at the network server, the list of target patients, wherein the list of target patients is ranked based at least in part on the matching index, wherein each target patient on the generated list is associated with at least one second healthcare professional;
   the network server providing an option to a first computer to communicate with any one of the at least one second healthcare professionals associated with the generated list of target patients; and
   based on a user selection of the option, the first healthcare professional sharing data related to the identified list of symptoms associated with the identified patient with the at least one second healthcare professional associated with the generated list of target patients.

2. The method of claim 1, wherein the identified list of symptoms comprises data representative of at least one symptom identified by a user.

3. The method of claim 1, wherein at least one target list of symptoms comprises data representative of at least one symptom associated with a target patient profile.

4. The method of claim 1, wherein the list of target patients comprises a list identifying patient profiles associated with symptoms similar to those symptoms identified in the identified list of symptoms.

5. The method of claim 1, further comprising:
   before receiving, at the network server, a request to generate the list of target patients, creating, at the network server, a patient profile, wherein the patient profile includes data representative of at least one symptom associated with the patient profile.

6. The method of claim 1, further comprising:
   generating, at the network server, a matching report, wherein the matching report includes the generated list of target patients, wherein the matching report includes a matching index for at least one target patient in the generated list, wherein the matching index comprises a numerical value representative of the similarity between the identified list of symptoms with the target list of symptoms.

7. The method of claim 6, wherein the matching report includes an identification of at least one second healthcare practitioner associated with a target patient on the generated list.

8. The method of claim 7, wherein the identification of the at least one second healthcare practitioner comprises data representative of contact information associated with the at least one second healthcare practitioner.

9. The method of claim 8, wherein the data representative of contact information is selected from the group consisting of a telephone number, email address, name, and mailing address.

10. The method of claim 6, wherein the matching report includes an identification of whether the at least one second healthcare practitioner is logged-in to the network server.

11. A system operable to facilitate the generation of a list of target patients, the system comprising:
   a network communication interface operable to send and receive messages;
   a processor;
   data storage; and
   program logic stored in the data storage and executable by the processor, to carry out functions comprising:
      receiving, at a network server, a request to generate the list of target patients, the request including an identified list of symptoms associated with an identified patient of a first healthcare professional;
      comparing, at the network server, at least one symptom from the identified list of symptoms against at least one target list of symptoms, wherein each target list of symptoms is associated with one target patient;

generating, at the network server, the list of target patients, including a matching index for at least one target patient in the generated list, wherein the matching index comprises a numerical value representative of the similarity between the identified list of symptoms with the target list of symptoms;

ranking, at the network server, the list of target patients, wherein the list of target patients is ranked based at least in part on the matching index, wherein each target patient on the generated list is associated with at least one second healthcare professional;

the network server providing an option to a first computer to communicate with any one of the at least one second healthcare professionals associated with the generated list of target patients; and based on a user selection of the option, the first healthcare professional sharing data related to the identified list of symptoms associated with the identified patient with the at least one second healthcare professional associated with the generated list of target patients.

12. A method comprising:

receiving, at a network server, a request to generate a list identifying target patients, the request including identified symptom data, wherein the identified symptom data is representative of at least one symptom associated with an identified patient of a first healthcare professional;

comparing, at the network server, the identified symptom data against at least one stored target symptom data, wherein the stored target symptom data is representative of a symptom associated with at least one target patient; and generating, at the network server, the list identifying target patients, including a matching index for at least one target patient in the generated list, wherein the matching index comprises a numerical value representative of the similarity between the identified list of symptoms with the target list of symptoms;

ranking, at the network server, the list of target patients, wherein the list identifying target patients is ranked based at least in part on the comparison;

generating a matching report, wherein the matching report includes the generated list identifying target patients, wherein each target patient on the generated list is associated with at least one second healthcare professional;

the network server providing an option to a first computer to communicate with any one of the at least one second healthcare professionals associated with the generated list of target patients; and based on a user selection of the option, the first healthcare professional sharing data related to the identified list of symptoms associated with the identified patient with the at least one second healthcare professional associated with the generated list of target patients.

13. The method of claim 12, wherein the generated report identifies a second healthcare practitioner for each target patient identified in the generated list of target patients.

* * * * *